US006906183B2

(12) United States Patent
Römisch et al.

(10) Patent No.: US 6,906,183 B2
(45) Date of Patent: Jun. 14, 2005

(54) PROCESS FOR THE SEPARATION OF GLYCOSYLATED AND NONGLYCOSYLATED PROTEINS

(75) Inventors: Jürgen Römisch, Marburg (DE); Jörg Weisse, Ebsdorfergrund (DE); Harald Stauss, Dauphetal (DE); Annette Feussner, Marburg (DE)

(73) Assignee: Delta Biotechnology Ltd., Nottingham (GB)

( * ) Notice: Subject to any disclaimer, the term of this patent is extended or adjusted under 35 U.S.C. 154(b) by 230 days.

(21) Appl. No.: 09/459,908

(22) Filed: Dec. 14, 1999

(65) Prior Publication Data

US 2002/0165367 A1 Nov. 7, 2002

(30) Foreign Application Priority Data

Dec. 18, 1998 (DE) .......................................... 198 58 777

(51) Int. Cl.[7] .............................. A23J 1/00; C07K 1/00
(52) U.S. Cl. ....................... 530/417; 530/363; 530/364; 530/412; 530/415; 530/413
(58) Field of Search ................................ 530/363, 412, 530/415, 364, 413, 417

(56) References Cited

U.S. PATENT DOCUMENTS 4,269,605 A    5/1981   Dean et al. .................... 436/67

OTHER PUBLICATIONS

Shaklaie, N. et al., J. Biol. Chem., vol. 259, No. 6, pp 3812–3817, 1984.*
Dean, Peter D.G., et al., "Protein Purification Using Immobilised Triazine Dyes," Journal of Chromatography, 165: 301–319 (1979).
C. R. Lowe, et al., "Some Preparative and Analytical Applications of Triazine Dyes," Int. J. Biochem, vol. 13: 33–40 (1981).
Tony Atkinson, et al., "Triazine–dye Affinity Chromatography," Biochemical Society Transactions, vol. 1: 290–293 (1981).
Richard L. Easterday, et al. "Affinity Chromatography of Kinases and Dehydrogenases on Sephadex® and Sepharose® Dye Derivatives," Plenum Press: 123–133 (1974).
E. Bisse and H. Wieland, "Coupling of m–aminophenylboronic acid to s–triazine–activiated Sephacryl: use in the affinity chromatography of glycated hemoglobins" *Journal of Chromatography* 575(2):223–228 (1992).
Y. Sakamoto, et al., "Stuctural study of the glycosylated and unglycosylated forms of a genetic variant of human serum albumin {63 Asp → Asn}" *Biochemica et Biophysica Acta* 1252(2):209–216 (1995).
L. Lin, "Betaseron" In: *Characterization of Biotechnology Pharmaceutical Products Dev. Biol. Stand.*, F. Brown, et al., Eds. 96:97–104 (1998).
T.W. Keenan and H.W. Heid, "Tight attachment of fatty acids to proteins associated with milk lipid globule membrane" *Eur. J. Cell Biol.* 26: 270–276 (1982).

* cited by examiner

*Primary Examiner*—Rebecca E. Prouty
*Assistant Examiner*—Delia M. Ramirez
(74) *Attorney, Agent, or Firm*—Finnegan, Henderson, Farabow, Garrett & Dunner, L.L.P.

(57) ABSTRACT

A process for the partial or complete separation of glycosylated and nonglycosylated proteins is described, in which: a) a triazine dye immobilized on a matrix is incubated with a mixture of glycosylated and nonglycosylated proteins, b) the matrix is then washed to remove the unbound proteins, and c) the proteins are eluted by means of a stepwise or continuous increase in the ionic strength or in the pH, nonglycosylated proteins and proteins having an increasing degree of glycosylation being collected separately from one another in the eluate fractions obtained. By means of the use of this process it is possible, for example, to prepare a human albumin which is free of glycoside bonds and is expressed in yeast cells.

11 Claims, 1 Drawing Sheet

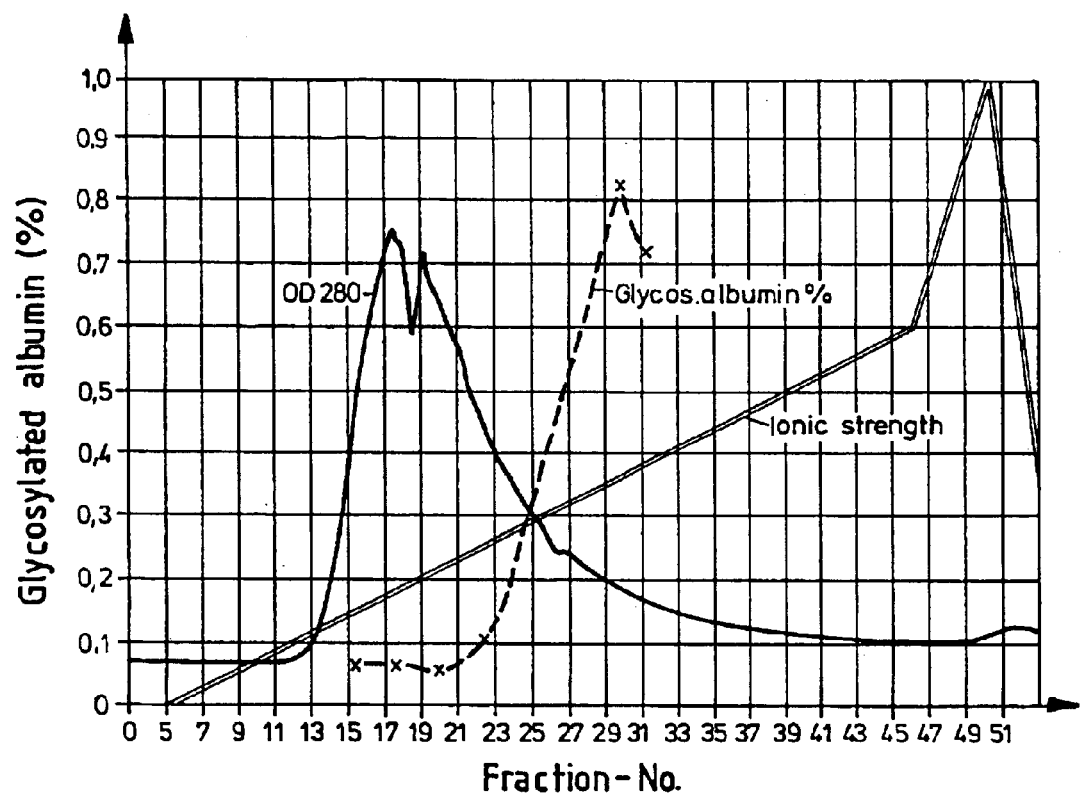

PROCESS FOR THE SEPARATION OF GLYCOSYLATED AND NONGLYCOSYLATED PROTEINS

The invention relates to a process for the chromatographic separation of glycosylated and non-glycosylated proteins.

It is known that the glycosylation of proteins, which proceeds intracellularly, serves physiologically for the stabilization of the proteins and their binding to cell receptors, which can play a role in cell activation processes. The nonenzymatic glycosylation of proteins can also occur extracellularly, such as is observed, for example, in the case of diabetes mellitus. Raised values of glycosylated albumin are frequently detected in the plasma of diabetic patients.

Glycosylations play a particular role in recombinant proteins. Thus a protein prepared in yeast cells, for example, which is completely identical to the amino acid sequence of the human protein, as a rule has a distinctly different glycosylation pattern if appropriate glycosylation sites are present. This can lead to a modified half-life of the recombinant protein, for example in the plasma, or to a formation of antibodies which, on repeated administration of the protein, can provoke allergic reactions.

In the expression of recombinant proteins, it is not unusually observed that only a part of the protein is glycosylated, which has to be detected and removed from the protein. However, there can also be cases in which the glycoslyated variant of the protein is the preferred product, from which the unglycosylated protein should be removed.

The separation of the glycosylated from the nonglycosylated variants of a protein can often be achieved only with great difficulty using the conventional methods such as chromatography or precipitation. The sugars which are linked N- or O-glycosidically to amino acids often change the physicochemical properties of the protein, such as the isoelectric point, only slightly, so that, for example, ion-exchange chromatography hardly helps. In German Patent Application 198 56 433.3, however, it has been described that immobilized lectins which recognize specific sugar structures can be helpful in the separation of glycoproteins and can be employed in certain test systems as an adsorbent or detection reagent. However, there is always the risk of "bleeding" of the matrix, as a result of which considerable interference can occur, for example, in biological tests, such as in cell cultures, owing to the released lectin. Since lectins can cause an immune reaction, their use for the production of medicaments which can be employed in man is not to be recommended.

A process for the partial or complete, chromatographic separation of glycosylated and nonglycosylated proteins has now been found, in which a) a triazine dye immobilized on a matrix is incubated with a mixture of glycosylated and nonglycosylated proteins, b) the matrix is then washed to remove the unbound proteins and c) the proteins are eluted by means of a stepwise or continuous increase in the ionic strength or in the pH, or the conditions are selected such that the glycosylated or the nonglycosylated protein passes through the matrix unbound and the respective bound protein is eluted, nonglycosylated proteins and proteins having an increasing degree of glycosylation being collected separately from one another in the eluate fractions obtained.

BRIEF DESCRIPTION OF THE DRAWING

FIG. 1 is a chromatogram depicting the separation of glycosylated human albumin from nonglycosylated human albumin on a Reactive Green 5-agarose column.

In fact, it is already known that dyes of the triazine series can be used for the separation of proteins from mixtures (1). These also include plasma proteins such as albumin or specific yeast proteins obtained from yeast extracts. A process for the separation of glycosylated and nonglycosylated constituents of a protein, however, is novel and surprising. As, for example, albumin expressed in yeasts or other eukaryotic cells is partially glycosylated, there is the necessity to have available a process for the separation of glycosylated albumin from non-glycosylated albumin. Moreover, in the production of recombinant proteins the cell proteins contained in the host cell extract are also obtained as contaminants, whose glycosylated constituents can likewise be removed using the process according to the invention. Thus it is known in the case of yeast proteins that the glycosylated proteins in particular, which often have mannose structures which are complex to a greater or lesser extent, can have an immunogenic effect in man even in low concentrations. Adequate removal of the glycosylated proteins from the protein intended for human use is thus necessary.

The triazine dyes to be employed according to the invention are, in particular, compounds from the group consisting of the CIBACRON® or PROCION® dyes. The methods for the covalent coupling of the triazine dyes to support materials such as agarose, crosslinked or non-crosslinked dextran, polyacrylamide or cellulose are also known to the person skilled in the art (2, 3, 4). The coupling processes are usually uncomplicated, rapid and do not include any toxic chemicals. The triazine dyes are distinguished by a high chemical stability, so that appropriate matrices can be used and stored over a long time. Dye matrices of this type also exhibit a high stability to proteolytic activity and other potential interfering effects. Moreover, the substances mentioned are comparatively inexpensive.

In the process according to the invention, the mixture of one or more proteins, which contains glycosylated and nonglycosylated variants of one or more proteins, is brought into contact with a triazine dye matrix, the matrix is washed and the proteins are then eluted. Gradients of increasing salt concentration are used for elution. Decreasing or increasing pH gradients are also suitable for continuous or stepwise elution. In the course of this, the proteins are separated from their glycosylated constituents and fractionated.

In a preferred embodiment of the process according to the invention, albumin is brought into contact with a dye matrix at a pH in the range between 3.5 and 10, washed and eluted stepwise or continuously by means of increasing salt concentration or increasing pH gradients. Conditions can also be chosen under which the respective glycosylated or nonglycosylated protein flows through the matrix unbound, which can be decided in each individual case according to the circumstances and influenced, for example, by means of the pH. A process is particularly preferred in which the albumin is contacted with an immobilized dye known as Reactive Green 5, preferably in the pH range from 6 to 10, particularly preferably in a phosphate buffer. After washing the matrix, the albumin freed of glycosylated protein is eluted by increasing the salt concentration. The glycosylated protein can than be recovered a further increase in the ionic strength.

The use of Reactive Yellow 3, which is preferably brought into contact with an albumin solution in the pH range from 3.5 to 6.5, is also particularly preferred. Here too, the separate elution of the glycosylated and the nonglycosylated albumins can be carried out by increasing the ionic strength and/or by increasing the pH.

Moreover, additives such as ethylene glycol or nucleotides can be used for elution. Also, other dye matrices such as CIBACRON® Blue can likewise be used. The invention is illustrated by the following example.

EXAMPLE

Under certain fermentation conditions, a small proportion of mannosylated albumin can be contained in human albumin expressed in transfected baker's yeast. This can be quantified as described in German Patent Application 198 56 433.3. In this process, the lectin concanavalin A is immobilized on a microtiter plate and serves as a scavenger for glycosylated molecules bearing mannose. Unbound, unglycosylated albumin is removed by washing and the bound albumin is determined by means of a labeled, monoclonal antibody fragment. A standard curve is used for quantification.

A sample prepared in this way was brought into a solution of 20 mM $Na_2HPO_4$, pH 7.0, by means of gel filtration and 70 mg of albumin were then applied to a Reactive Green 5 agarose column (Sigma; diameter: 1.6 cm, height 10cm). After washing the column with the abovementioned buffer, an NaCl gradient (0.1 M; gradient 0.2%/ml) was applied and fractions of 7.5 ml each were collected. The albumin concentration in each sample was quantified by means of SEC-HPLC by integrating the peak areas and reading off the content on a standard curve. The contents of glycosylated albumin were determined as described above. The ratio of glycosylated protein to total protein was expressed in percent.

The result can be seen from the chromatogram attached as FIG. 1. It shows the course of the absorption at 280 nm, i.e. especially the protein passing through the photometer. In addition, the continuous salt gradient is documented by measurement of the ionic strength. The calculated percentage proportion of glycosylated albumin of the albumin detectable in the fraction (dashed line) was subsequently recorded. It is clear to see that the fractions 13 to 22 contained a significantly decreased content of glycosylated protein compared with the starting material (0.52%). On the other hand, clearly increased contents of the glycosylated albumin were found in fraction 30 (about 0.8%) and in the pool of fractions 50 to 53 (1.34%).

Overall, a clear effect of separation of glycosylated and non-glycosylated albumin is seen, which can be further optimized, for example, by applying a flatter salt gradient.

BIBLIOGRAPHY (1) Dean P. D. G., Watson D. H., *J. Chromatogr.* 1979; 165:302–319;
(2) Lowe C. R. et al., *Int. J. Biochem.* 1981; 13:33–40;
(3) Atkinson T. et al., *Biochem. Soc. Trans.,* 1981; 9:290–293;
(4) Easterday R. L. et al., *Adv. Exp. Med. Biol.* 1974; 42:123–133.

What is claimed:

1. A process for the partial or complete separation of a mixture of glycosylated and nonglycosylated variants of a protein, wherein the glycosylated variants bear mannose, which comprises
   a) incubating a triazine dye immobilized on a matrix with the mixture of glycosylated and nonglycosylated variants,
   b) washing the matrix with a buffer to remove the unbound variants,
   c) eluting the variants from the matrix by means of a stepwise or continuous increase in the ionic strength or in the pH of the buffer, and
   d) collecting nonglycosylated variants and variants having an increasing degree of glycosylation separately from one another in the eluate fractions obtained.

2. The process of claim 1, wherein the matrix consists of agarose, crosslinked or noncrosslinked dextran, polyacrylamide or cellulose.

3. The process of claim 1, wherein one or more compounds from the group consisting of Reactive Green 5, Reactive Blue 2, and Reactive Yellow 3 are employed as triazine dyes.

4. The process of claim 1, wherein the mixture of glycosylated and nonglycosylated variants is incubated with the triazine dye matrix at a pH of between 3.5 and 10.

5. The process of claim 1, wherein the nonglycosylated variants have been separated from glycosylated variants.

6. The process of claim 5, wherein the glycosylated and nonglycosylated variants have been prepared recombinantly in eukaryotic cells or in transgenic microorganisms.

7. The process of claim 5, wherein the protein is human albumin expressed in yeast cells.

8. The process of claim 6, wherein the eukaryotic cells are yeast cells.

9. The process of claim 3, wherein the mixture of glycosylated and nonglycosylated variants is incubated with Reactive Green 5 at a pH of between 6 and 10.

10. The process of claim 3, wherein the mixture of glycosylated and nonglycosylated variants is incubated with Reactive Yellow 3 at a pH of between 3.5 and 6.5.

11. The process of claim 3, wherein the mixture of glycosylated and nonglycosylated variants is incubated with Reactive Blue 2.

* * * * *